US008852113B2

(12) United States Patent
Nishina et al.

(10) Patent No.: US 8,852,113 B2
(45) Date of Patent: Oct. 7, 2014

(54) SPECIMEN COLLECTION TREATMENT INSTRUMENT

(71) Applicant: Olympus Medical Systems Corp., Tokyo (JP)

(72) Inventors: Kenichi Nishina, Hachioji (JP); Takuya Imahashi, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/735,150

(22) Filed: Jan. 7, 2013

(65) Prior Publication Data

US 2013/0123623 A1    May 16, 2013

Related U.S. Application Data

(63) Continuation of application No. PCT/JP2012/063675, filed on May 28, 2012.

(30) Foreign Application Priority Data

Jul. 6, 2011 (JP) ................. 2011-150330

(51) Int. Cl.
*A61B 8/12* (2006.01)
*A61B 10/02* (2006.01)
*A61B 8/00* (2006.01)

(52) U.S. Cl.
CPC ............. *A61B 10/0266* (2013.01); *A61B 8/00* (2013.01); *A61B 8/12* (2013.01); *A61B 8/445* (2013.01); *A61B 10/0275* (2013.01)
USPC .......................................... 600/466; 600/562

(58) Field of Classification Search
USPC ................................. 600/466, 562
See application file for complete search history.

(56) References Cited

U.S. PATENT DOCUMENTS

| 4,634,420 A | * | 1/1987 | Spinosa et al. ........... 604/22 |
| 5,106,364 A | | 4/1992 | Hayafuji et al. |

(Continued)

FOREIGN PATENT DOCUMENTS

| JP | 08-024259 | 1/1996 |
| JP | 2004-216159 | 8/2004 |

(Continued)

OTHER PUBLICATIONS

European Search Report dated Aug. 23, 2013 from corresponding European Application No. 12 80 7447.3.

*Primary Examiner* — Tse Chen
*Assistant Examiner* — Angela M Hoffa
(74) *Attorney, Agent, or Firm* — Scully, Scott, Murphy & Presser, P.C.

(57) ABSTRACT

In a distal end portion of a flexible sheath which is inserted integrally with an ultrasound transducer array, cell collecting hole portions each including a through-hole which allows a distal end portion outer periphery and an internal space of the flexible sheath to communicate with each other is provided, an edge for specimen cutting is formed at an opening portion of an outer circumferential side of each of the cell collecting hole portions, and after the flexible sheath is caused to reach a lesion part or the like of a subject, specimen collection is performed without additionally inserting a biological forceps or the like into the flexible sheath, whereby a specimen of a target site such as a lesion part is reliably collected without unnecessarily increasing the number of times of insertion and extraction of an instrument into and from a body, and the burden on an examinee is reduced.

4 Claims, 13 Drawing Sheets

(56) References Cited

U.S. PATENT DOCUMENTS

| | | | |
|---|---|---|---|
| 6,261,242 B1* | 7/2001 | Roberts et al. | 600/564 |
| 6,299,622 B1 | 10/2001 | Snow et al. | |
| 6,986,748 B2* | 1/2006 | McAlister et al. | 600/564 |
| 7,828,745 B2* | 11/2010 | McAlister et al. | 600/566 |
| 7,862,517 B2* | 1/2011 | Tsonton et al. | 600/567 |
| 8,262,587 B2* | 9/2012 | Mcalister et al. | 600/567 |
| 2005/0090765 A1* | 4/2005 | Fisher | 600/570 |
| 2005/0119652 A1 | 6/2005 | Vetter et al. | |
| 2009/0287080 A1* | 11/2009 | Nishina et al. | 600/439 |
| 2010/0063392 A1* | 3/2010 | Nishina et al. | 600/439 |
| 2010/0063401 A1* | 3/2010 | Nishina et al. | 600/466 |
| 2010/0256499 A1* | 10/2010 | Imahashi | 600/459 |
| 2011/0077674 A1* | 3/2011 | Sullivan et al. | 606/170 |
| 2011/0196404 A1* | 8/2011 | Dietz et al. | 606/169 |
| 2011/0288412 A1* | 11/2011 | Deckman et al. | 600/439 |
| 2012/0078094 A1* | 3/2012 | Nishina et al. | 600/431 |
| 2012/0179178 A1* | 7/2012 | Simpson | 606/159 |
| 2012/0265057 A1* | 10/2012 | Nishina et al. | 600/424 |
| 2013/0041259 A1* | 2/2013 | Harks et al. | 600/439 |
| 2013/0102925 A1* | 4/2013 | McGhie | 600/567 |
| 2013/0109974 A1* | 5/2013 | Nishina et al. | 600/461 |

FOREIGN PATENT DOCUMENTS

| | | |
|---|---|---|
| JP | 2010-274123 | 12/2010 |
| WO | 2007/062406 A2 | 5/2007 |

\* cited by examiner

SPECIMEN COLLECTION TREATMENT INSTRUMENT

CROSS REFERENCE TO RELATED APPLICATION

This application is a continuation application of PCT/JP2012/063675 filed on May 28, 2012 and claims benefit of Japanese Application No. 2011-150330 filed in Japan on Jul. 6, 2011, the entire contents of which are incorporated herein by this reference.

BACKGROUND OF THE INVENTION

1. Field of the Invention

The present invention relates to a specimen collection treatment instrument suitable to collect a specimen of a target site by being inserted into a body of a subject.

2. Description of the Related Art

Conventionally, as a method for diagnosing a lesion part or the like in a body, specimen collection has been known. When specimen collection is performed, a target site in which the lesion part or the like is present is identified first, after which, a specimen of the target site is collected and specimen collection is performed.

Identification of the target site is performed with use of an ultrasound probe as disclosed in, for example, Japanese Patent Application Laid-Open Publication No. 2004-216159. Namely, an ultrasound probe is inserted into a body, and based on an ultrasound signal received with an ultrasound transducer provided at a distal end portion thereof, the target site is identified. In this case, for example, an ultrasound probe is fitted in a tube-shaped sheath, and the ultrasound probe and the tube-shaped sheath are both inserted into the body, and after the target site is identified with the ultrasound probe, the ultrasound probe is extracted in a state in which the tube-shaped sheath is indwelling in the site.

Next, a specimen collection treatment instrument such as a specimen collection forceps, brush or the like is inserted into the tube-shaped sheath, a distal end portion of the specimen collection treatment instrument is guided to the target site along the tube-shaped sheath, and a specimen such as a lesion tissue or a cell of the target site is collected. In this case, it is confirmed under X-ray observation whether or not the distal end of the specimen collection treatment instrument reaches the target site.

SUMMARY OF THE INVENTION

A specimen collection treatment instrument according to one aspect of the present invention includes a tubular portion insertable into a body, a cell collecting hole portion including a through-hole which allows a distal end portion outer periphery and an internal space of the tubular portion to communicate with each other, an edge for specimen cutting that is formed at an opening portion of an outer circumferential side of the cell collecting hole portion, a rod portion that is inserted in the tubular portion, and is advanceable and retractable with respect to the tubular portion mutually, and an ultrasound observation section disposed at a distal end of the rod portion.

DETAILED DESCRIPTION OF THE PREFERRED EMBODIMENTS

Figure 1:
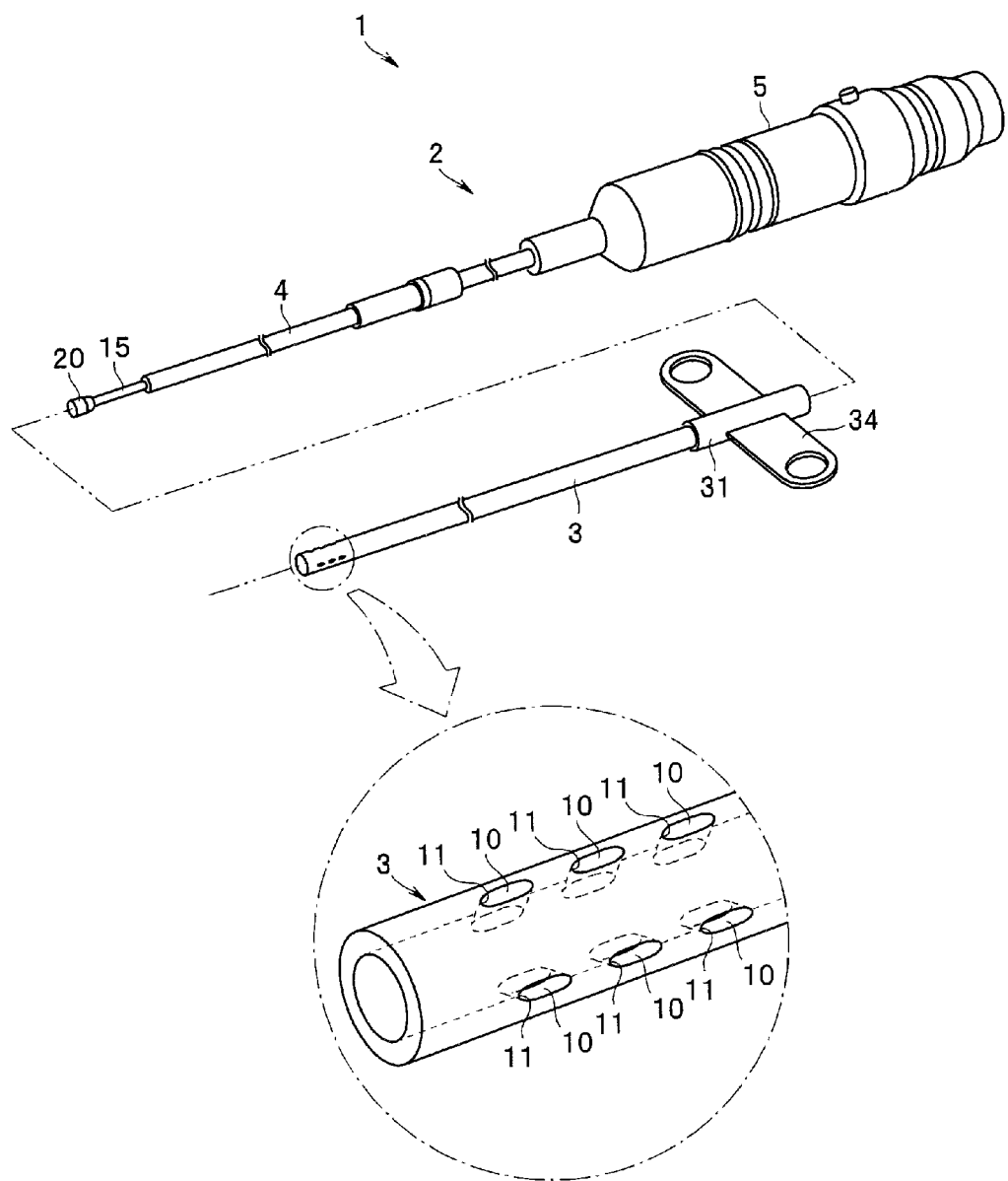
FIG. 1 is a perspective view of a specimen collection treatment instrument according to a first embodiment of the present invention.
Figure 2:
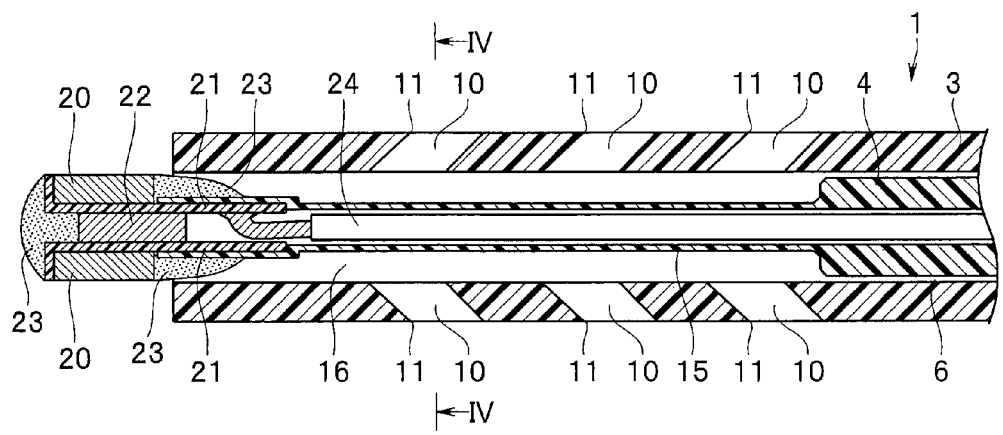
FIG. 2 is a sectional view of a distal end portion of the specimen collection treatment instrument at a time of a rod portion being advanced according to the first embodiment of the present invention.
Figure 3:
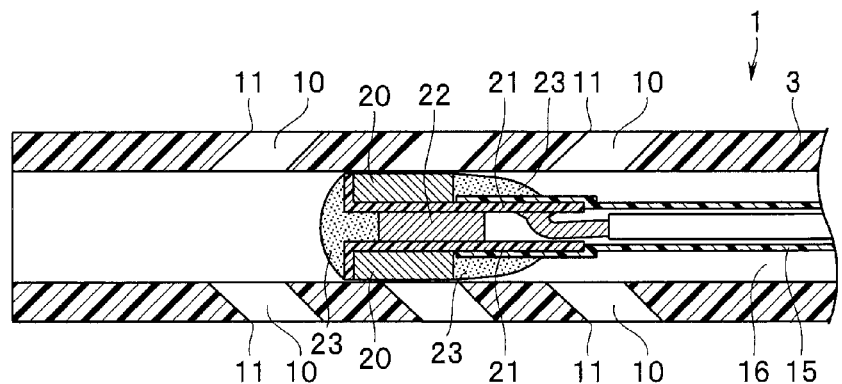
FIG. 3 is a sectional view of the distal end portion of the specimen collection treatment instrument at a time of the rod portion being retracted according to the first embodiment of the present invention.
Figure 4:
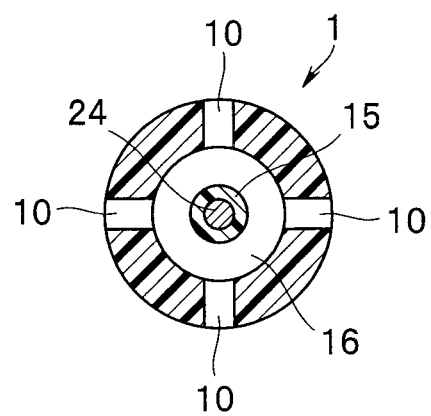
FIG. 4 is a sectional view taken along the IV-IV line of FIG. 2 according to the first embodiment of the present invention.
Figure 5:
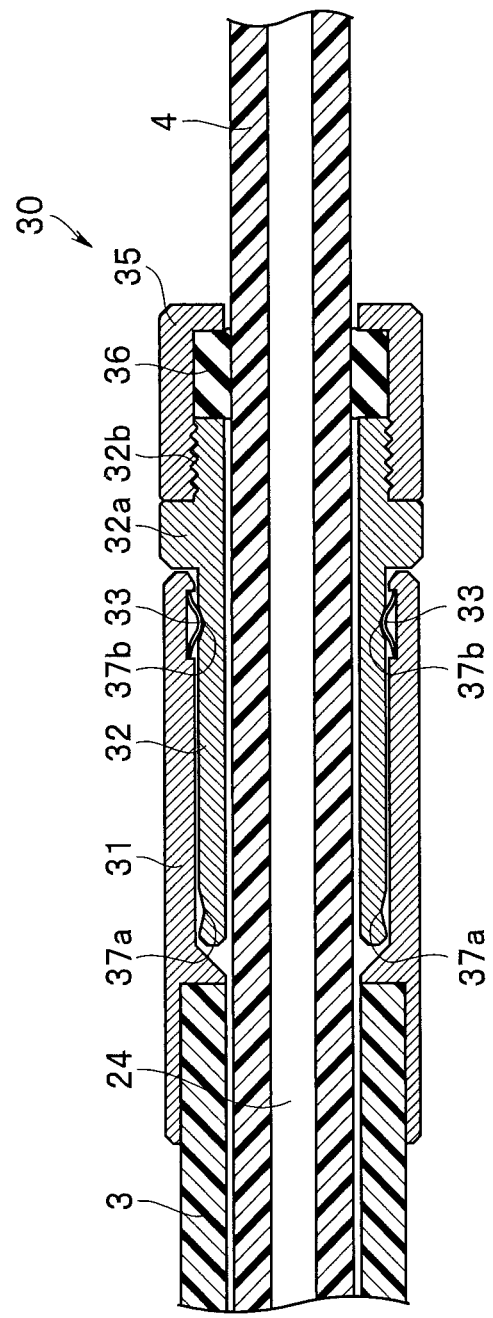
FIG. 5 is a sectional view of a hand slide mechanism at the time of the rod portion being advanced according to the first embodiment of the present invention.
Figure 6:
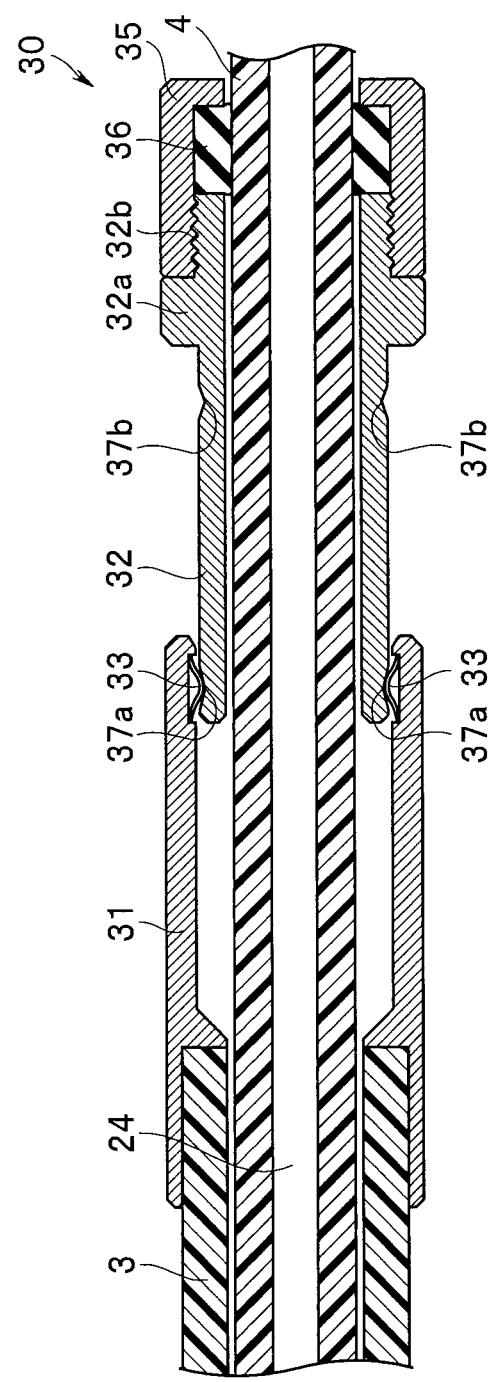
FIG. 6 is a sectional view of the hand slide mechanism at the time of the rod portion being retracted, according to the first embodiment of the present invention.
Figure 7:
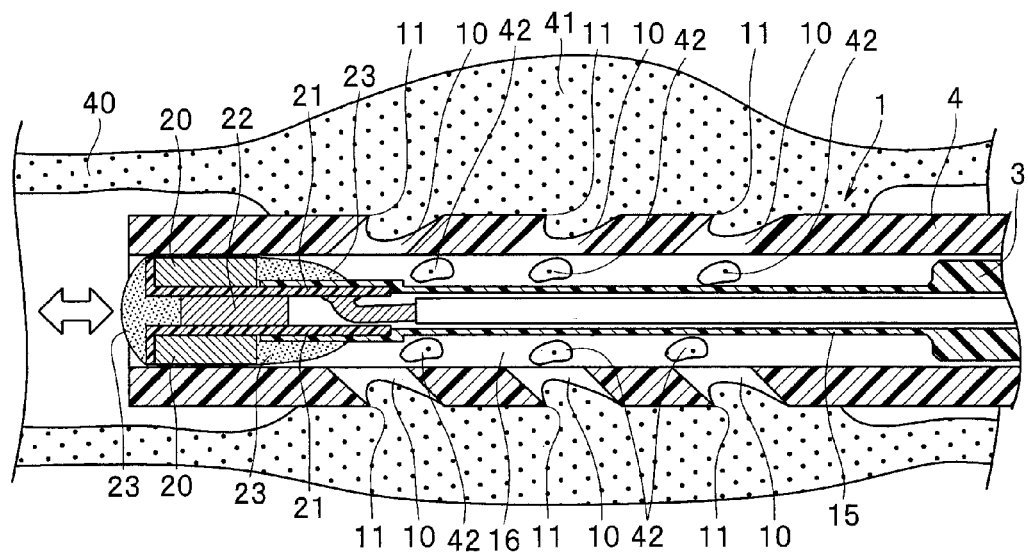
FIG. 7 is an explanatory view showing specimen collection of a lesion part in an inside of a peripheral bronchus, according to the first embodiment of the present invention.
Figure 8:
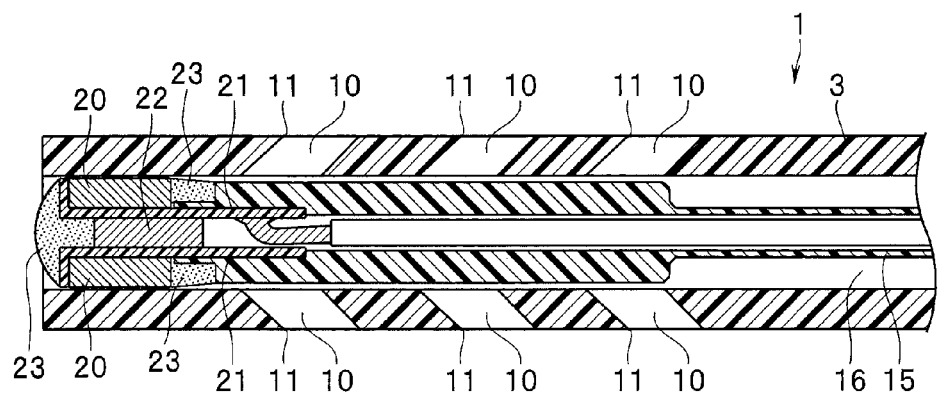
FIG. 8 is a sectional view showing a first modification of the distal end portion of the specimen collection treatment instrument according to the first embodiment of the present invention.
Figure 9:
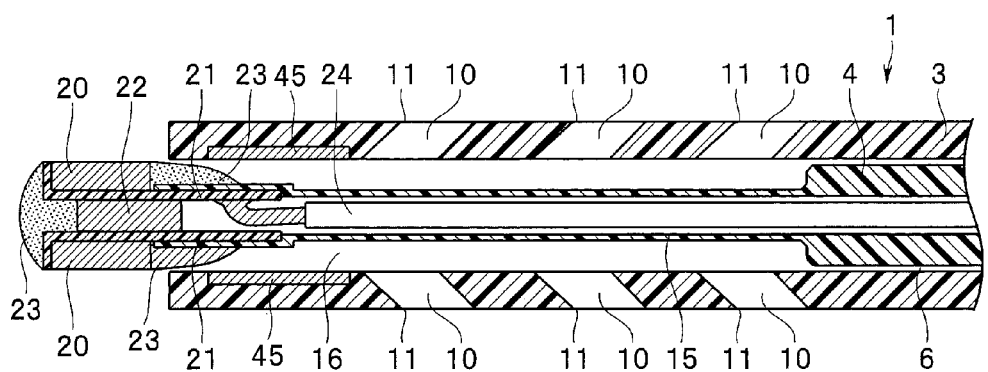
FIG. 9 is a sectional view showing a second modification of the distal end portion of the specimen collection treatment instrument according to the first embodiment of the present invention.
Figure 10:
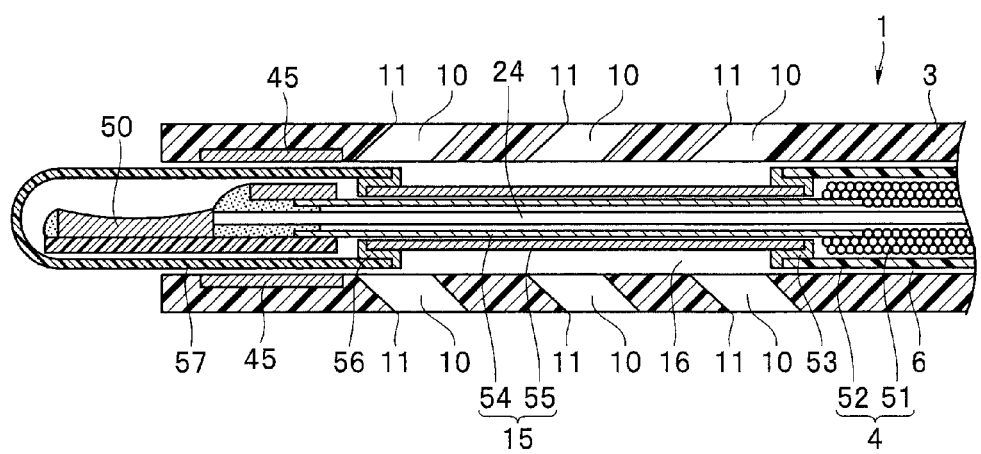
FIG. 10 is a sectional view showing a third modification of the distal end portion of the specimen collection treatment instrument according to the first embodiment of the present invention.
Figure 11:
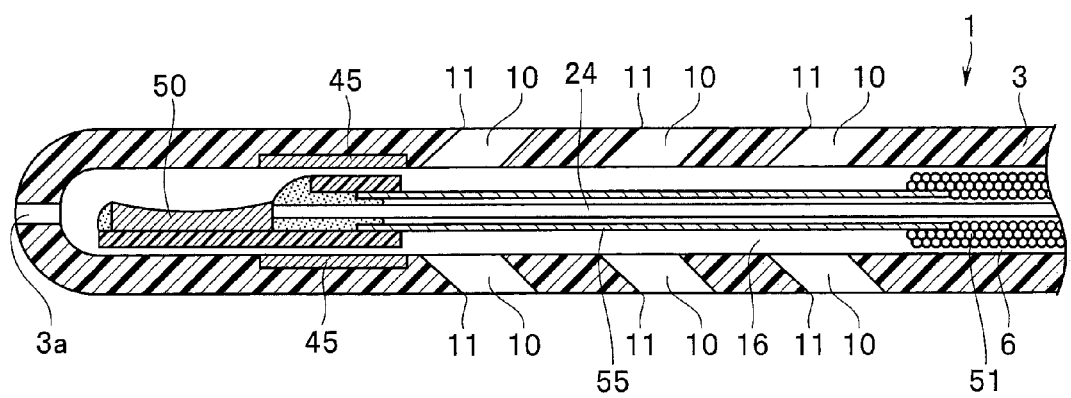
FIG. 11 is a sectional view showing a fourth modification of the distal end portion of the specimen collection treatment instrument according to the first embodiment of the present invention.

Hereinafter, embodiments of the present invention will be described with reference to the drawings. FIG. 1 to FIG. 11 relate to a first embodiment of the present invention. FIG. 1 is a perspective view of a specimen collection treatment instrument. FIG. 2 is a sectional view of a distal end portion of the specimen collection treatment instrument at a time of a rod portion being advanced. FIG. 3 is a sectional view of the distal end portion of the specimen collection treatment instrument at a time of the rod portion being retracted. FIG. 4 is a sectional view taken along the IV-IV line of FIG. 2. FIG. 5 is a sectional view of a hand slide mechanism at the time of the rod portion being advanced. FIG. 6 is a sectional view of the hand slide mechanism at the time of the rod portion being retracted. FIG. 7 is an explanatory view showing a state in which a specimen is collected from specimen collection of a lesion part in an inside of a peripheral bronchus. FIG. 8 is a sectional view showing a first modification of the distal end portion of the specimen collection treatment instrument. FIG. 9 is a sectional view showing a second modification of the distal end portion of the specimen collection treatment instrument. FIG. 10 is a sectional view showing a third modification of the distal end portion of the specimen collection treatment instrument. FIG. 11 is a sectional view showing a fourth modification of the distal end portion of the specimen collection treatment instrument. Note that the drawings are schematic, the relation of the thicknesses and the widths of the respective members, the ratio of the thickness of the respective members and the like differ from the actual relation, ratio and the like, and the portions which differ from one another in the size relation and the ratio are included among the drawings as a matter of course.

A specimen collection treatment instrument 1 shown in FIG. 1 has a treatment instrument main body 2, and a flexible sheath 3 as a tubular portion. Further, the treatment instrument main body 2 has a rod portion 4 that is long, and has a small diameter and flexibility, and a connector portion 5 which can be connected to an ultrasound observation apparatus not illustrated is provided at a proximal end portion of the rod portion 4. The specimen collection treatment instrument 1 of the present embodiment is favorably used in specimen collection in extremely small-diameter lumens such as a peripheral bronchus of a lung or the like, a pancreas duct and a bile duct. The size is not especially limited, and can be properly set in accordance with purposes. For example, an outside diameter of the flexible sheath 3 may be approximately 2 [mm], and an outside diameter of the rod portion 4 may be approximately 1.4 [mm].

The flexible sheath 3 has a plurality of cell collecting hole portions 10 including through-holes which allows a distal end portion outer periphery and an internal space to communicate with each other. More specifically, as shown in, for example, FIG. 1 to FIG. 4, at a distal end portion of the flexible sheath 3, for example, four hole portion groups each with the three cell collecting hole portions 10 arranged in an insertion axis direction as one group are disposed at each of equal rotational angles along a circumferential direction.

In the present embodiment, the cell collecting hole portion 10 is configured by a long hole which exists extensively in the insertion axis direction of the flexible sheath 3, and penetrates through the flexible sheath 3 from an outer circumferential side to an inner circumferential side as the cell collecting hole portion 10 is inclining to a distal end side. Namely, the cell collecting hole portion 10 of the present embodiment is configured by a through-hole with a sectional shape thereof along the insertion axis direction forming a parallelogram. Thereby, an angle which is formed by a distal end side of the cell collecting hole portion 10 and an outer circumferential face of the flexible sheath 3 is formed to be an acute angle, and a site formed at the acute angle is set as an edge 11 for specimen cutting.

Here, the flexible sheath 3 is configured by a resin material having ultrasound transmissivity such as a polymer resin or a fluorine resin, for example. As the resin material that configures the flexible sheath 3, for example, a polymer resin such as polyethylene, a polyamide, and polyurethane can be favorably adopted, and among the materials, rigid polyethylene is especially preferably adopted.

The rod portion 4 is inserted through the flexible sheath 3 in a state in which the rod portion 4 is relatively advanceable and retractable, and between an inner periphery of the flexible sheath 3 and an outer periphery of the rod portion 4, a slide portion 6 which reduces frictional resistance at a time of both of the flexible sheath 3 and the rod portion 4 being relatively moved in an axial direction is provided. In the present embodiment, a low frictional coefficient layer or layers is or are formed by using a material which does not affect a human body, at one or both of the inner surface of the flexible sheath 3 and an outer circumferential face of the rod portion 4, and the low frictional coefficient layer is set as the slide portion 6.

Relative slide described here may be any one of sliding the slide portion 6 back and forth with the insertion portion 4 being fixed, sliding the insertion portion 4 back and forth with the slide portion 6 being fixed, and sliding both of the insertion portion 4 and the slide portion 6.

Further, when the flexible sheath 3 and the insertion portion 4 are configured by PTFE, polyethylene or the like with favorable slidability, the slide portion 6 may be formed by only a suitable clearance being provided without formation of the low frictional coefficient layer.

The rod portion 4 is a long shaft having flexibility, and a thin portion 15 which is in a thinner state than other portions is formed at a part of a distal end side of the rod portion 4 as shown in FIGS. 2 and 3. More specifically, in the present embodiment, the thin portion 15 is formed by a diameter of a distal end portion of the rod portion 4 being reduced. The thin portion 15 has a length of at least an arrangement length of the cell collecting hole portions 10 of the respective groups arranged on the flexible sheath 3, and forms a specimen housing chamber 16 inside the flexible sheath 3. For example, when the rod portion 4 is located in a predetermined advancing position with respect to the flexible sheath 3 as shown in FIG. 2, the specimen housing chamber 16 is allowed to communicate with the respective cell collecting hole portions 10, and can house specimens (which will be described later) that are collected through the cell collecting hole portions.

The thin portion 15, that is, a surface of the specimen housing chamber 16 increases in holding capability of a tissue, and preferably has lipophilicity. Further, in facilitating advance and retract in a tubular portion, a surface of the thin portion 15 preferably has lipophilicity as compared with a tubular portion inner surface.

As means that makes the surface of the thin portion 15 lipophilic, means that coats a lipophilic resin, means that forms the thin portion from a lipophilic resin and the like are cited.

Further, at a distal end (that is, a distal end of the thin portion 15) of the rod portion 4, an electrostatic capacitance type ultrasound transducer array (ring array) 20 as an ultrasound observation section is disposed. The ultrasound transducer array 20 is, for example, c-MUT (capacitive-micromachined ultrasonic transducers) which is produced with use of, for example, a micro machine production process, and by the ultrasound transducer array 20, an ultrasound tomographic image by, for example, radial electronic scanning can be obtained. Further, besides an electrostatic capacitance type ultrasound transducer, a piezoelectric type ultrasound transducer can be also used.

As shown in FIGS. 2 and 3, a bottom surface of the ultrasound transducer array 20 is mounted on outer circumferential face of a flexible printed circuit (FPC: flexible printed circuits) 21 which is formed into a cylindrical shape. Further, an integrated circuit element (IC) 22 as a circuit element which processes an ultrasound signal which is transmitted and received at the ultrasound transducer array 20 is mounted on inner surfaces of the flexible printed circuit 21. A proximal portion side of the flexible printed circuit 21 mounted with the ultrasound transducer array 20 and the integrated circuit element 22 like this is inserted into a distal end portion of the thin portion 15 and are fixed via fillers 23 or the like.

Furthermore, in the thin portion 15, one end of a lead wire 24 is electrically connected to the flexible printed circuit 21. Further, the other end side of the lead wire 24 is inserted through the inside of the rod portion 4 and is extended to the connector portion 5 provided on the proximal end, side. The connector portion 5 is connected to an ultrasound observation apparatus not illustrated, whereby supplying of a power source to a flexible printed circuit 21 side from the ultrasound observation apparatus, exchanging of signals between the flexible printed circuit 21 and the ultrasound observation apparatus, and the like are performed.

In the present embodiment, the integrated circuit element 22 functions as a waveform shaping circuit which shapes a waveform of the ultrasound signal received at the ultrasound transducer array 20 (or functions as an amplifying circuit which amplifies the ultrasound signal which is received), and functions as a multiplexer which sequentially switches a plurality of transducers which configure the ultrasound transducer array 20. Thereby, the diameter of the lead wire 24 can be reduced.

Here, an outside diameter of the ultrasound transducer array 20 is formed to be an outside diameter which allows the ultrasound transducer array 20 to be inserted into the flexible sheath 3 (namely, is formed to be substantially the same diameter as the outside diameter of the rod portion 4), whereby the ultrasound transducer array 20 can move to advance and retract inside the flexible sheath 3 by accompanying relative movement of the flexible sheath 3 and the rod portion 4. In this case, advancing and retracting movement of the ultrasound transducer array 20 is performed by, for example, operating a hand slide mechanism 30 which is provided between the flexible sheath 3 and the rod portion 4.

As shown in FIGS. 1, 5 and 6, the hand slide mechanism 30 has a slide operation section 31 which is fixedly provided at a proximal end portion of the flexible sheath 3, and a slider 32 which is fixedly provided at a midpoint of a proximal portion side of the rod portion 4.

The slide operation section 31 is configured by, for example, a substantially cylindrical member, and is fixedly provided by a distal end side being fitted on a proximal end portion of the flexible sheath 3. Further, a spring portion 33 which projects in a bow shape, for example, is provided at a proximal end side inner periphery of the slide operation section 31. Further, a finger rest portion 34 is projectingly provided at an outer circumferential side of the slide operation section 31 (see FIG. 1).

The slider 32 is configured by a substantially cylindrical member having an outward flange 32a at a proximal portion side. A male screw portion 32b is formed on an outer periphery of the proximal portion side from the outward flange 32a on the slider 32, and a fixing pipe sleeve 35 is screwed onto the male screw portion 32b. A rubber tube 36 is sandwiched between the fixing pipe sleeve 35 and a proximal end of the slider 32, an inner surface of the rubber tube 36 is pressed against an outer circumferential face of the rod portion 4 by screwing of the fixing pipe sleeve 35, whereby the slider 32 is fixed to a desired position on the rod portion 4, whereas a distal end side from the outward flange 32a, of the slider 32 is capable of being loosely fitted into the slide operation section 31. On an outer periphery of the distal end side of the slider 32, an engaging recessed portions 37a and 37b which can be selectively engaged with the spring portion 33 are provided at two spots at a front and a rear.

For example, as shown in FIG. 5, when the slider 32 is slid (forced in) to a front side with respect to the slide operation section 31, and the spring portion 33 is engaged in the engaging recessed portion 37b at the distal end side, the rod portion 4 is positioned to a predetermined advanced position with respect to the flexible sheath 3. Thereby, for example, as shown in FIG. 2, the ultrasound transducer array 20 is projected from the distal end of the flexible sheath 3, and all the cell collecting hole portions 10 are opened into the specimen housing chamber 16.

On the other hand, when the slider 32 is slid rearward (drawn out) with respect to the slide operation section 31 as shown in FIG. 6, for example, and the spring portion 33 is engaged in the engaging recessed portion 37a at the proximal portion side, the rod portion 4 is positioned to a predetermined retracted position with respect to the flexible sheath 3. Thereby, the ultrasound transducer array 20 is retracted into the flexible sheath 3 as shown in FIG. 3, for example.

The slider 32 can also be extracted from the slide operation section 31, and thereby, the rod portion 4 can be extracted from the flexible sheath 3 in accordance with necessity.

Next, a use mode of the specimen collection treatment instrument 1 which includes the configuration as above will be described. First, a surgeon or the like connects the connector portion 5 which is provided at a proximal end side of the treatment instrument main body 2 to the ultrasound observation apparatus.

When the connector portion 5 of the specimen collection treatment instrument 1 is connected to the ultrasound observation apparatus, an ultrasound drive signal is outputted from the ultrasound observation apparatus, and the ultrasound drive signal is inputted in a multiplexer which is provided in the integrated circuit element 22 via the lead wire 24. The multiplexer receives the ultrasound drive signal, sequentially drives the respective transducers of the ultrasound transducer array 20 which is provided at the distal end of the rod portion 4, and performs ultrasound scanning by ultrasounds emitted from the respective transducers.

Next, the rod portion 4 of the treatment instrument main body 2, and the flexible sheath 3 which is sheathed over the rod portion 4 are inserted through the inside of a body. At the time, the slider 32 is slid forward with respect to the slide operation section 31 of the hand slide mechanism 30, and the spring portion 33 is engaged in the engaging recessed portion 37b at the distal end side, whereby the ultrasound transducer array 20 is held in a state in which the ultrasound transducer array 20 is projected from the distal end of the flexible sheath 3, and favorable ultrasound observation is enabled.

Incidentally, the distal end of the rod portion 4 is provided with a radiopaque marker not illustrated, and therefore, it can be properly confirmed how far the distal end of the rod portion 4 is inserted, in an x-ray fluoroscopic image or a CT image.

Subsequently, when the distal end of the rod portion 4 reaches the vicinity of a target site, a surgeon or the like performs positioning of the cell collecting hole portions 10 on the flexible sheath 3, with respect to a lesion part 41 (see FIG.

7) in a tube passage 40 while the surgeon or the like observes an ultrasound image. Note that when mucus or the like of a region of interest can be used as an ultrasound medium at a time of ultrasound observation, ultrasound observation can be performed without contact with mucosa.

In this case, the flexible sheath 3 has ultrasound transmissivity, and an ultrasound image at a predetermined level can be also observed through the flexible sheath 3. Accordingly, after the surgeon or the like confirms the lesion part 41 by the ultrasound transducer array 20 which is projected from the flexible sheath 3, for example, the surgeon or the like relatively moves the slider 32 with respect to the slide operation section 31 of the hand slide mechanism 30, retracts the ultrasound transducer array 20 into the flexible sheath 3, fine-tunes the position of the flexible sheath 3 while the surgeon or the like observes the ultrasound image through the flexible sheath 3, and thereby can position the cell collecting hole portions 10 to the lesion part 41 in the tube passage 40 in real time with high precision.

Subsequently, when positioning of the cell collecting hole portions 10 to the lesion part 41 is performed, the surgeon or the like performs positioning of the rod portion 4 to the flexible sheath 3 so that the respective cell collecting hole portions 10 face the specimen housing chamber 16, and thereafter, moves the flexible sheath 3 minutely backward and forward a plurality of times together with the rod portion 4 (see FIG. 7). Thereby, part of the stenosed lesion part 41 is shaved off by the edges 11 formed at the cell collecting hole portions 10, and the shaved and collected lesion parts are housed into the specimen housing chamber 16 through the cell collecting hole portions 10 as a specimen 42.

According to the embodiment as above, the distal end portion of the flexible sheath 3 which is inserted integrally with the ultrasound transducer array 20 is provided with the cell collecting hole portions 10 each including the through-hole which allows the distal end portion outer periphery and the internal space of the flexible sheath 3 to communicate with each other, and the edges 11 for specimen cutting are further formed at the opening portions of the outer circumferential sides of the cell collecting hole portions 10, whereby after the flexible sheath 3 is caused to reach the lesion part 41 or the like of the subject, specimen collection can be performed without a biological forceps or the like being additionally inserted into the flexible sheath 3. Accordingly, the specimen 42 of the target site of the lesion part 41 or the like is reliably collected without the number of times of insertion and extraction of the instrument into and from the body being increased more than necessary, and the burden on an examinee can be reduced.

In this case, the rod portion 4 of the present embodiment has the ultrasound transducer array 20 at the distal end of the thin portion 15, and the specimen housing chamber 16 is configured by a space which is closed at the front and the rear, in the flexible sheath 3. Accordingly, if the rod portion 4 is extracted from the flexible sheath 3 after collecting operation of the specimen 42 is performed in the lesion part 41, the specimen 42 housed in the specimen housing chamber 16 can be taken outside the body while the flexible sheath 3 is left in the body. Subsequently, if the flexible sheath 3 is extracted from the inside of the body after it is confirmed that the specimen 42 is collected, the operation of inserting the flexible sheath 3 into the body again can be omitted even if collection of the specimen ends in failure, and the burden on the subject can be reduced.

Further, if the flexible sheath 3 is configured by a disposable component, the effect of eliminating necessity of cleaning/disinfecting or the like of the cell collecting hole portions 10 configured by very small through-holes is provided.

Here, concerning the configurations of the rod portion 4, the ultrasound observation section and the like, various changes can be made. For example, as shown in FIG. 8, in place of the configuration in which the thin portion 15 is formed at the distal end of the rod portion 4, the thin portion 15 can be also formed at a position which is retracted to the proximal end side by a predetermined length from the distal end of the rod portion 4. If the thin portion 15 is formed as above, the respective cell collecting hole portions 10 can be closed by the distal end portion of the rod portion 4 at the time of insertion and extraction of the flexible sheath 3, and cells and the like other than the desired specimen 42 can be prevented from being included into the specimen housing chamber 16. Further, as shown in, for example, FIG. 9, at the distal end portion of the flexible sheath 3, a ring-shaped shielding portion 45 that shields the distal end portion from ultrasound can be also provided. If the configuration like this is adopted, an ultrasound image can be temporarily discontinued by the shielding portion 45 when the rod portion 4 is relatively moved with respect to the flexible sheath 3. Subsequently, the position where the ultrasound image is discontinued (that is, the position where the shielding portion 45 is disposed) is set as a reference, whereby even when flexure or the like occurs to midpoints of the flexible sheath 3 and the rod portion 4, a relative position of the distal end portions of the flexible sheath 3 and the rod portion 4 can be grasped with high precision. Further, the flexible sheath 3 may be formed from a material with which ultrasound is blocked instead of being provided with the shielding portion 45.

Further, as shown in FIG. 10, for example, in place of the ultrasound transducer array 20, a mechanical scan type ultrasound observation section including an ultrasound transducer 50 of a single plate can be also adopted. In the modification, for example, the rod portion 4 is configured with a flexible shaft 51 covered with a sheath large diameter portion 52 as a main body, and the thin portion 15 is configured by having a sheath small diameter portion 55 connected to a distal end of the sheath large diameter portion 52 via a pipe sleeve 53. Further, a distal end cap 57 is connected to a distal end portion of the sheath small diameter portion 55 via a pipe sleeve 56. Furthermore, a small diameter shaft 54 having a proximal end side thereof connected to the flexible shaft 51 is inserted through an inside of the sheath small diameter portion 55. The ultrasound transducer 50 which is housed in the distal end cap 57 is connected to a distal end portion of the small diameter shaft 54.

Further, as shown in FIG. 11, for example, the distal end portion of the flexible sheath 3 can be closed, with a small hole 3a being left. FIG. 11 shows a configuration in which the flexible shaft 51 and the small diameter shaft 54 are not covered with a sheath large diameter portion and a sheath small diameter portion. According to the configuration like this, the distal end portion of the rod portion 4 is butted to the distal end portion of the flexible sheath 3, whereby distal end positions of the flexible sheath 3 and the rod portion 4 can be easily grasped. Further, for example, an ultrasound medium (physiological saline or the like) is poured into the flexible sheath 3 from a user's hand side, and is discharged from the small hole 3a, whereby the medium can be supplied onto the transducer without the mediation of air bubbles or the like.

Figure 12:
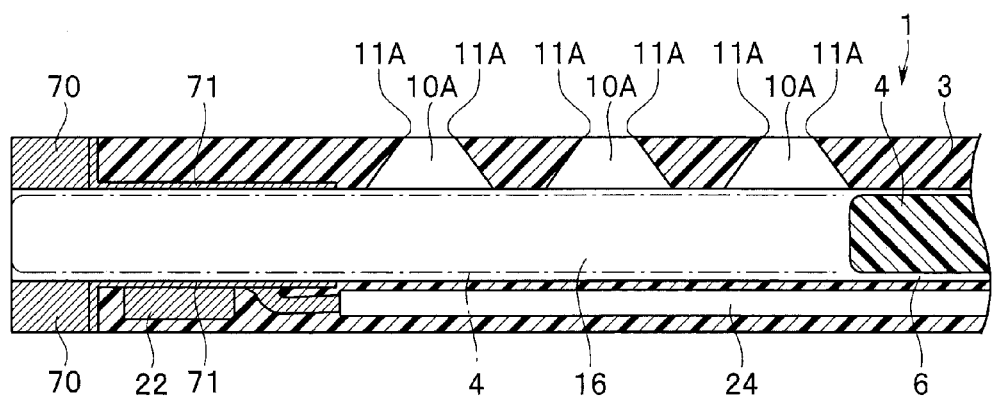
FIG. 12 is a sectional view of a distal end portion of a specimen collection treatment instrument according to a second embodiment of the present invention.
Figure 13:
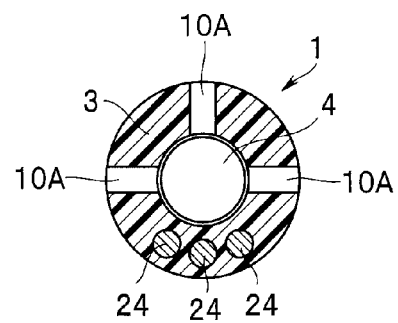
FIG. 13 is a sectional view taken along the XIII-XIII line of FIG. 12, according to the second embodiment of the present invention.
Figure 14:
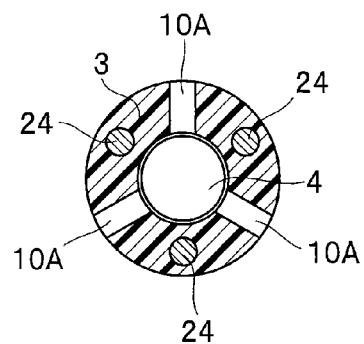
FIG. 14 is a sectional view showing a modification of FIG. 13, according to the second embodiment of the present invention.
Figure 15:
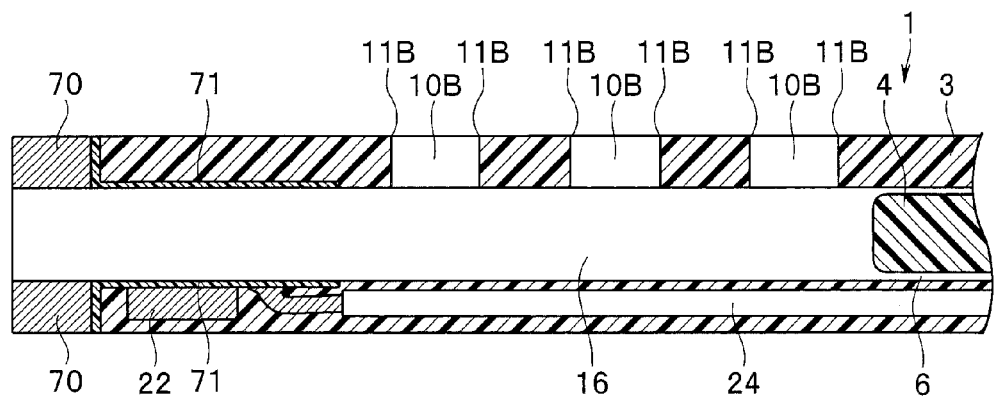
FIG. 15 is a sectional view showing a first modification of the specimen collection treatment instrument according to the second embodiment of the present invention.
Figure 16:
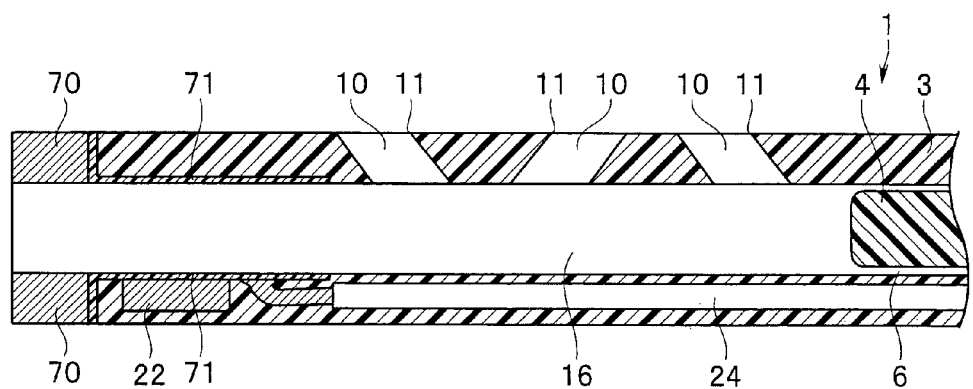
FIG. 16 is a sectional view showing a second modification of the specimen collection treatment instrument according to the second embodiment of the present invention.
Figure 17:
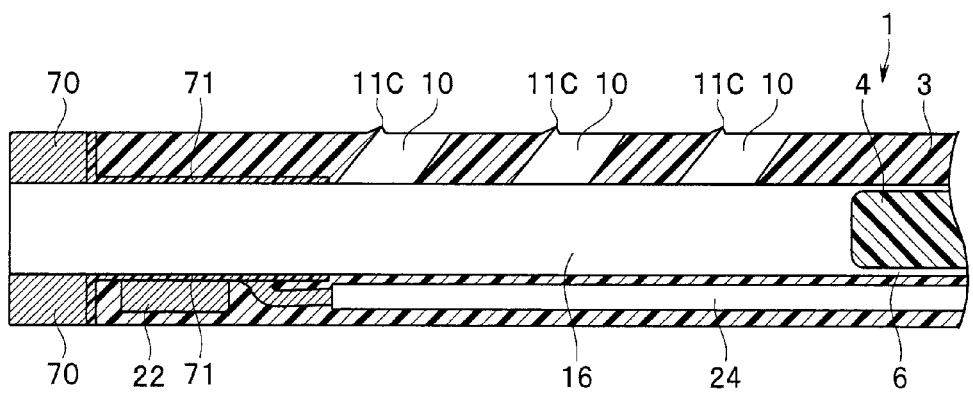
FIG. 17 is a sectional view showing a third modification of the specimen collection treatment instrument according to the second embodiment of the present invention.
Figure 18:
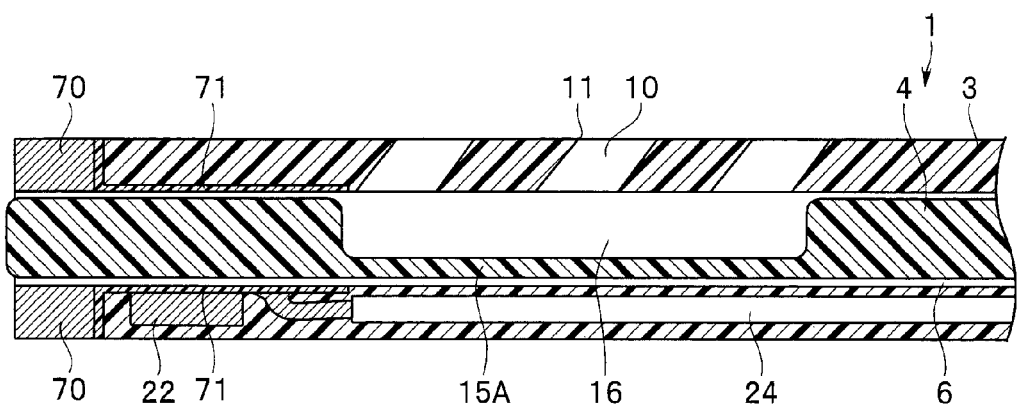
FIG. 18 is a sectional view showing a fourth modification of the specimen collection treatment instrument according to the second embodiment of the present invention.
Figure 19:
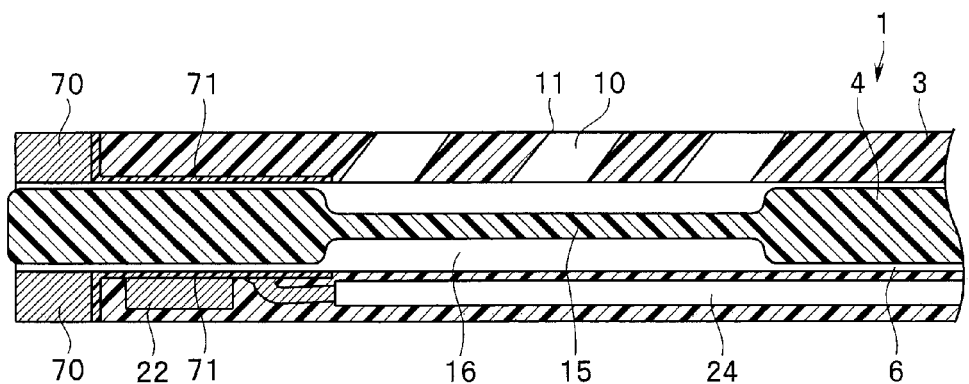
FIG. 19 is a sectional view showing a fifth modification of the specimen collection treatment instrument according to the second embodiment of the present invention.
Figure 20:
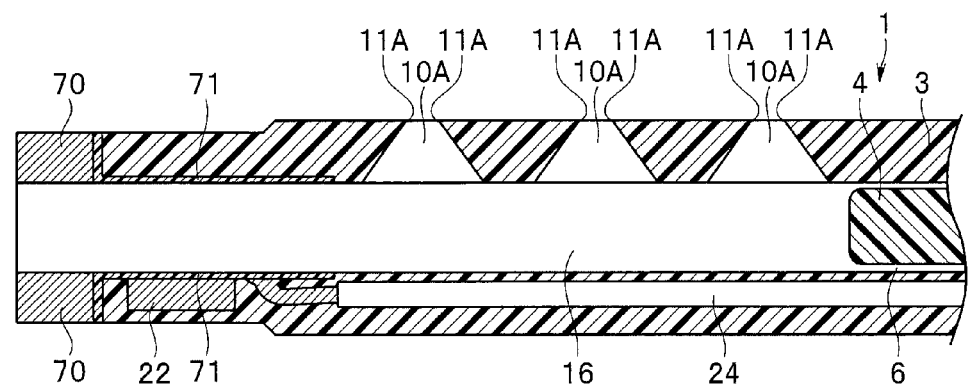
FIG. 20 is a sectional view showing a sixth modification of the specimen collection treatment instrument according to the second embodiment of the present invention.

Next, FIG. 12 to FIG. 20 relate to a second embodiment of the present invention. FIG. 12 is a sectional view of a distal end portion of a specimen collection treatment instrument. FIG. 13 is a sectional view taken along the XIII-XIII line of FIG. 12. FIG. 14 is a sectional view showing a modification of FIG. 13. FIG. 15 is a sectional view showing a first modification of the specimen collection treatment instrument. FIG. 16 is a sectional view showing a second modification of the specimen collection treatment instrument. FIG. 17 is a sectional view showing a third modification of the specimen collection treatment instrument. FIG. 18 is a sectional view showing a fourth modification of the specimen collection treatment instrument. FIG. 19 is a sectional view showing a fifth modification of the specimen collection treatment instrument. FIG. 20 is a sectional view showing a sixth modification of the specimen collection treatment instrument. Here, the present embodiment mainly differs from the first embodiment described above in the point in which an ultrasound observation section is provided at a flexible sheath side. Note that the same components as in the first embodiment described above are assigned with the same reference signs, and the description thereof will be omitted.

As shown in FIG. 12, in the present embodiment, an ultrasound transducer array 70 is disposed at the distal end portion of the flexible sheath 3 via a flexible printed circuit 71. When the flexible printed circuit 71 is explained more specifically, the flexible printed circuit 71 is formed into a substantially cylindrical shape with a distal end side folded outward, for example. In the flexible printed circuit 71, a proximal portion side in a substantially cylindrical shape is fixedly provided on a distal end portion inner periphery of the flexible sheath 3, and the ultrasound transducer array 70 is mounted on a distal end face which is formed by being folded outward. Further, the integrated circuit element 22 which is buried in the distal end portion of the flexible sheath 3 is mounted on the flexible printed circuit 71, and one end of the lead wire 24 buried along the insertion axis direction of the flexible sheath 3 is electrically connected to the flexible printed circuit 71. The other end side of the lead wire 24 is provided to extend to the proximal end side of the flexible sheath 3, and is connectable to the ultrasound observation apparatus via the connector portion (none is illustrated).

Further, in the distal end portion of the flexible sheath 3, at the proximal portion side from the ultrasound transducer array 70, a plurality of cell collecting hole portions 10A including through-holes which allows the outer periphery and the internal space of the flexible sheath 3 to communicate with each other are provided. More specifically, as shown in, for example, FIGS. 12 and 13, for example, three hole portion groups with three cell collecting hole portions 10A arranged in the insertion axis direction set as one group are disposed at each of equal rotational angle positions at 90 degrees with one side in which the lead wire 24 is buried as a starting point. For example, as shown in FIG. 14, the cell collecting hole portions 10A of the respective groups can be disposed at each of the equal rotational positions alternately with the lead wires 24.

In the present embodiment, the cell collecting hole portion 10A is configured by a long hole with a sectional shape thereof forming a substantially trapezoid tapering toward an outer circumferential side from an inner circumferential side, for example. Thereby, the angles which are formed by a distal end side and a rear end side of the cell collecting hole portion 10A and the outer circumferential face of the flexible sheath 3 are formed to be acute angles, and sites which are formed at the acute angles are set as edges 11A for specimen cutting.

As shown in FIGS. 12 and 13, the rod portion 4 is a long shaft having flexibility. An outside diameter thereof is formed to have a uniform thickness from the distal end side to the proximal end side. In this case, the rod portion 4 is retracted to the proximal portion side, whereby the specimen housing chamber 16 with a distal end opened is formed in the flexible sheath 3. The specimen which is housed in the specimen housing chamber 16 can be taken out from a distal end opening portion of the flexible sheath 3 by the rod portion 4 being advanced to the distal end side of the flexible sheath 3 (see the dashed line in FIG. 12) after the flexible sheath 3 and the rod portion 4 are extracted outside the body.

According to the above configuration, in addition to the substantially same operational effect as in the first embodiment described above, the ultrasound transducer array 70 is disposed at the flexible sheath 3 side, whereby the disposition space of the ultrasound transducer array 70 can be easily secured especially in the diameter direction. Accordingly, for example, when the ultrasound transducer array having the same outside diameter is used, an insertion diameter as the entire specimen collection treatment instrument 1 can be significantly reduced as compared with the configuration in which the ultrasound transducer array is disposed at the rod portion 4.

Further, the outside diameter of the rod portion 4 is formed to be the same diameter from the distal end side to the proximal end side, whereby the rod portion 4 can be made to go along the inside of the flexible sheath 3 uniformly, and occurrence of buckling and the like at the time of insertion into the body can be reduced.

Here, concerning the configurations of the flexible sheath 3, the rod portion 4 and the like, various modifications can be made. For example, as shown in FIG. 15 to FIG. 17, the mode of the cell collecting hole portions which are formed in the flexible sheath 3 can be variously modified.

For example, as shown in FIG. 15, a cell collecting hole portion 10B can be also formed by a through-hole which is orthogonal to the outer circumferential face of the flexible sheath 3. In this case, for example, a front portion and a rear portion of the cell collecting hole portion 10B function as edges 11B.

Further, for example, as shown in FIG. 16, the cell collecting hole portions 10 which include through-holes with sections in substantially parallelograms shown in the first embodiment described above can be disposed in a state in which perforating directions are made to differ alternately. Furthermore, for example, as shown in FIG. 17, edges 11C can be raised in the outer circumferential direction of the flexible sheath 3.

Other than the above, various modifications can be made with respect to the mode of the cell collecting hole portion. In this case, the edge for specimen cutting is desirably formed to be an acute angle, but the edge is not restricted to this, and if only the angle of the edge is within the range of an angle of 95 degrees or less, for example, the specimen can be favorably cut.

Further, for example, as shown in FIG. 18, a configuration can be adopted, in which a recessed portion is formed at a distal end side midpoint of the rod portion 4, whereby a thin portion 15A is formed, and by the thin portion 15A, the specimen housing chamber 16 is formed in the flexible sheath 3.

Alternately, for example, as shown in FIG. 19, the distal end side midpoint of the rod portion 4 is formed to have a small diameter, whereby the thin portion 15 is formed, and by the thin portion 15, the specimen housing chamber 16 can be also formed in the flexible sheath 3.

Further, for example, as shown in FIG. 20, in the flexible sheath 3, at least an outside diameter of a site where the cell collecting hole portions 10A are formed can be made larger than an outside diameter of the distal end side from the site. By adoption of the configuration, the cell collecting hole portions 10A can be reliably brought into contact with mucosa and the like while insertability of the flexible sheath 3 is secured by the site at the distal end side which is formed to have a small diameter, for example.

Note that the present invention is not limited to the respective embodiments, the respective modifications and the like described above, and can be properly changed within the range without departing from the gist of the present invention, as a matter of course. For example, part of the configurations described in the embodiments (and modifications) described above can be properly replaced with part of the other embodiment (and modifications) and the like.

What is claimed is:

1. A specimen collection treatment instrument, comprising:
    a tubular portion adapted to be inserted into a body;
    a cell collecting hole portion comprising a through-hole which allows a distal end portion outer periphery and an internal space of the tubular portion to communicate with each other;
    an edge for specimen cutting that is formed to be at an acute angle by a surface forming an inner periphery of the cell collecting hole portion and a surface of the tubular portion;
    a rod portion that is inserted in the tubular portion, and is advanceable and retractable with respect to the tubular portion mutually, the rod portion comprising a cylindrical thin portion as a narrower portion of the rod portion, a diameter of the thin portion being smaller than a diameter of a portion longitudinally adjacent to the thin portion, the thin portion adapted to house a specimen that is collected through the cell collecting hole portion, wherein the diameter of the thin portion is centered about the diameter of the portion longitudinally adjacent to the thin portion; and
    an ultrasound observing section disposed at a distal end of the rod portion, the ultrasound observing section comprising an ultrasound transducer that transmits ultrasound for obtaining an ultrasound tomographic image through the tubular portion and receives reflected ultrasound,
    wherein the thin portion is arranged adjacent to the ultrasound observing section.

2. The specimen collection treatment instrument according to claim 1,
    wherein the tubular portion has ultrasound transmissivity.

3. The specimen collection treatment instrument according to claim 2,
    wherein at a part of a distal end side of the tubular portion, a shielding portion which shields the part of the distal end side from ultrasound is disposed.

4. The specimen collection treatment instrument according to claim 2,
    wherein in the rod portion, at least a surface of the thin portion includes a hydrophobic portion with high lipophilicity as compared with an inner surface of the tubular portion.

* * * * *